(12) United States Patent
Detinkin et al.

(10) Patent No.: US 7,256,883 B2
(45) Date of Patent: Aug. 14, 2007

(54) METHOD FOR THE OPTICAL INSPECTION OF A TRANSPARENT PROTECTIVE LAYER AND OF A COLORED PATTERNED SURFACE

(75) Inventors: Igor Detinkin, Constance (DE); Hans-Peter Diehl, Constance (DE); Robert Massen, Am Rebberg 29, Ohningen-Wangen (DE) 78337

(73) Assignee: Robert Massen, Ohningen-Wangen (DE)

( * ) Notice: Subject to any disclaimer, the term of this patent is extended or adjusted under 35 U.S.C. 154(b) by 124 days.

(21) Appl. No.: 10/542,531

(22) PCT Filed: Jan. 15, 2004

(86) PCT No.: PCT/EP2004/000251

§ 371 (c)(1),
(2), (4) Date: Jul. 15, 2005

(87) PCT Pub. No.: WO2004/065947

PCT Pub. Date: Aug. 5, 2004

(65) Prior Publication Data

US 2006/0114463 A1    Jun. 1, 2006

(30) Foreign Application Priority Data

Jan. 19, 2003   (DE) ................................ 103 01 931

(51) Int. Cl.
*G01N 21/00*   (2006.01)
(52) U.S. Cl. .................... 356/237.1; 356/317
(58) Field of Classification Search ............... 356/300, 356/237.1–237.2, 237.4–237.5, 239.8, 430–431, 356/317; 250/234–235, 223 B, 359.1
See application file for complete search history.

(56) References Cited

U.S. PATENT DOCUMENTS

| | | | | |
|---|---|---|---|---|
| 4,725,139 A | * | 2/1988 | Hack et al. | 356/237.1 |
| 5,374,988 A | * | 12/1994 | Wertz et al. | 356/328 |
| 5,459,330 A | | 10/1995 | Venaille et al. | |
| 6,319,349 B1 | * | 11/2001 | Lin | 156/206 |
| 6,375,776 B1 | * | 4/2002 | Buoni et al. | 156/209 |
| 6,809,809 B2 | * | 10/2004 | Kinney et al. | 356/237.5 |
| 6,879,390 B1 | * | 4/2005 | Kvamme et al. | 356/237.2 |
| 2002/0135758 A1 | | 9/2002 | Jarlath et al. | |
| 2003/0011760 A1 | | 1/2003 | Wells et al. | |
| 2003/0160968 A1 | * | 8/2003 | Deck | 356/515 |

* cited by examiner

*Primary Examiner*—Gregory J. Toatley, Jr.
*Assistant Examiner*—Tri Ton
(74) *Attorney, Agent, or Firm*—Stuart J. Friedman (57) ABSTRACT

A method for the optical inspection of a transparent protective layer and a colored patterned surface which is at least partially covered by the transparent protective layer involves providing a source of illumination and an imaging sensor associated with the source of illumination and illuminating the protective layer with light emitted by the source of illumination in order to recognize defective places inside and beneath the transparent protective layer. The source of illumination emits light in the shortwaved range which is at least partially diffuse and the light striking the surface penetrates at least partially into the protective layer and is scattered at the defective places. Light scattered from the defective places is picked up by the imaging sensor and the defective places are recognized by the local increase in the intensity of the light picked up by the imaging sensor in the area of the defective places.

23 Claims, 4 Drawing Sheets

METHOD FOR THE OPTICAL INSPECTION OF A TRANSPARENT PROTECTIVE LAYER AND OF A COLORED PATTERNED SURFACE

The present invention relates to a method for the optical inspection of a transparent protective layer and of a colored patterned surface, whereby the transparent protective layer at least partially covers the colored patterned surface, said method using a first source of illumination as well as an imaging sensor associated with the first source of illumination.

The present invention also relates to an arrangement for the optical inspection of a transparent protective layer and of a colored patterned surface, in which the transparent protective layer at least partially covers the colored patterned surface, which comprises a first source of illumination whose emission spectrum encompasses shortwaved visible light, as well as an imaging sensor associated with the first source of illumination.

The automatic optical inspection of smooth, multi-colored surfaces using special cameras, illumination means and pattern-recognition as well as image-processing computers is already known from many production sectors such as, for example, the ceramics industry or the wood industry.

It is likewise a known procedure to detect these surfaces simultaneously using different cameras and illumination systems so as to recognize esthetic defects in the coloration (contamination, color discrepancies, etc.) as well as physical defects on the surface (lumps, scratches, irregularities, gloss defects). A typical technique is detection with one or more color cameras under diffuse incident illumination and with one or more separate black-and-white cameras that pick up light from a source of illumination that is directed onto and reflected off the surface.

German patent specification DE 196 09 045 C1 describes a refinement to a so-called multi-sensorial camera for the inspection of wooden specimens in which the various cameras and sources of illumination no longer observe the surface at different places but rather, they use a shared lens system to scan the same place on the surface that is illuminated by different sources of illumination and observed by different image sensors that are each associated with respective sources of illumination.

The optical checking has the objective not only of segregating defective products or of assigning the products to certain quality classes, but also of displaying the different defect classes, in order to provide the machine operator with the information he needs to adjust the production process so as to reduce the defects. For this purpose, it is necessary not only to detect the defects but also to classify them, that is to say, to identify the detected defects.

The prior-art systems, however, are not capable of achieving this objective satisfactorily in the case of surfaces having single-colored or multi-colored patterns that are provided with a transparent protective layer. These include, for example, multi-colored laminate floor coverings in which a decoratively printed film with a wood grain, stone pattern or other decor is laid onto a substrate made of fiberboard and then one or more transparent, so-called overlay films are applied onto this film. These overlay films can be made, for example, of a mixture or melamine and corundum and they ensure the friction-resistance, hardness and water-tightness of the floor covering.

There are also laminate floors where a multi-colored printed plastic film is applied onto a plastic substrate and this arrangement, in turn, is provided with one or more transparent but strong protective layers. Likewise known are surfaces where the transparent protective layer is applied in liquid form and then hardens. Below, all of these surfaces will be combined under the general term "laminates".

The optical inspection is rendered more difficult due to the fact that many laminate floors are provided with an embossed structure in order to simulate the surface properties of natural materials such as wood and natural stone. As a result, the surface of the protective layer is no longer smooth.

When it comes to these laminates, the known arrangements for optical inspection of the transparent protective layers and of colored patterned surfaces using color cameras and associated diffuse incident illumination as well as black-and-white cameras that pick up the reflected light from a directed source of incident illumination are limited to the recognition of color defects and mismatches in the decor as well as to the recognition of the physical defects in the transparent protective layer.

However, these arrangements are not capable of recognizing slight defects inside the transparent protective layer and of identifying them as such.

The undirected reflection of the diffuse incident illumination is markedly modulated by the colored decor film, but hardly by typical defects inside the transparent protective layer such as, for example, slight milkiness or localized tears in the protective layer. Although a mild milky transparency slightly changes the saturation of the color decors that are to be inspected, due to the efforts to make the decor look as realistic as possible, the decor prints have a wide band-width of saturation values, so that a weak saturation caused by the milkiness of the protective layer cannot be distinguished from the intentional saturation differences that are present in the decor print.

The black-and-white camera that picks up the light from a directed source of incident illumination that is reflected off the surface can detect local defects in the gloss and in the integrity of the surface. However, this illumination hardly penetrates into the transparent protective layer and is thus changed only slightly or not at all as a result of defects inside the protective layer. Moreover, many laminate floor coverings are produced mechanically with surface patterns that are embossed into the protective layer. In this case, a camera system that observes by means of reflection is virtually unable to detect defects inside the protective layer. Even major defects in the protective layer such as, for example, complete local tears in the transparent protective layer, are not reliably recognized.

Therefore, the known systems for optical inspection of laminates can only detect some of the production defects and then they can only insufficiently identify the detected production defects. In view of the large quantities of surfaces produced worldwide, there is great economic interest in a method for the optical inspection of surfaces by means of which—in addition to the defects in the decor and on the surface of the transparent protective layer—defects inside the transparent protective layer can also be reliably recognized at the same time.

According to the present invention, in order to recognize defective places inside and beneath the transparent protective layer, the protective layer is illuminated with the light emitted by the source of illumination, whereby the source of illumination emits light in the shortwaved visible range and the light striking the surface penetrates at least partially into the protective layer and is scattered at the defective places. Light scattered back from the defective places is picked up by the imaging sensor and the defective places are recognized by the local increase in the intensity of the light picked up by the imaging sensor in the area of the defective places. The shorter the wavelength of the light, the larger the fraction of the light scattered at the defective places, so that a source of illumination is selected whose emission spectrum encompasses the shortwaved visible range. In this manner, defective places inside the protective layer can be reliably recognized.

In order to minimize the influence of the embossing of the surface, according to a preferred embodiment of the method, the source of illumination and the imaging sensor associated with the source of illumination are arranged perpendicularly above the surface of the transparent protective layer.

In accordance with another preferred embodiment of the method according to the invention, a second source of illumination is provided that emits light at a first wavelength that excites the protective layer to fluoresce with light at a second wavelength that is different from the first wavelength. The fluorescent light is picked up by an imaging sensor associated with the second source of illumination. Defective places in the transparent protective layer are then recognized on the basis of local changes in the intensity of the fluorescent light since, for example, in areas where there is no protective layer at all, no fluorescent light is picked up by the imaging sensor. In order to pick up the fluorescent light, the imaging sensor associated with the second source of illumination preferably has greater sensitivity in the wavelength range of the second wavelength than in the wavelength range of the first wavelength. As a result, when the imaging sensor is, for example, a black-and-white camera, places with an intact protective layer appear brighter than places where there is no protective layer.

According to another preferred embodiment of the method, the same source of illumination is employed in order to excite the fluorescent light and to recognize defective places inside the transparent protective layer by means of the scatter at the defective places. For instance, so-called black-light lamps, which have an ultraviolet fraction that excites the fluorescence of the protective layer and which also emit a shortwaved visible fraction, can be employed to illuminate the material to be inspected. In this manner, a single source of illumination and a single camera can use the localized higher scatter to recognize the milkiness defects as bright colored image places inside the transparent protective layer, and they can use the localized absence of fluorescence to recognize the localized absence of the transparent protective layer as dark image places on the overall slightly bright background.

In another preferred embodiment of the method, color-capable imaging sensors are employed in addition to the imaging sensor(s) that pick up the fluorescent light or the back-scattered light, whereby said color-capable imaging sensors detect color defects in the colored patterned surface that is at least partially covered by the transparent protective layer. In addition to this, in order to detect defects on the surface of the transparent protective layer, a third source of illumination can be provided which emits a directed beam of light that is reflected off the surface of the protective layer and that is picked up by an imaging sensor associated with the third source of illumination. Defects on the surface can then be recognized on the basis of local changes in the intensity of the reflected light picked up by the imaging sensor. As a result, all of the defects on the surface of the protective layer can be detected that either reflect the illuminating beam of light at an angle other than the angle of incidence (for instance, bumps or dents) or that reflect the beam of light at the same angle but with a different intensity (for example, places that are locally too dull or too glossy).

The present invention also provides an arrangement for the optical inspection of surfaces with which defects inside the transparent protective layer can be reliably recognized.

In accordance with the arrangement according to the invention, there is a first source of illumination whose emission spectrum encompasses shortwaved visible light and an imaging sensor associated with the first source of illumination, whereby the imaging sensor picks up light scattered back from the defective places inside and beneath the transparent protective layer, and whereby the imaging sensor can recognize the defective places on the basis of the local increase in the intensity of the light picked up by the imaging sensor in the area of the defective places.

Additional features and advantages of the invention can be gleaned from the subordinate claims as well as from the description below of several preferred embodiments which are depicted in the accompanying drawings. These show the following:

Hereinafter, the term "color channel" refers to the arrangement of a color camera and a diffusely radiating source of illumination, while "reflection channel" refers to the arrangement of a black-and-white camera and a source of illumination with a directed beam of light, while "overlay channel" refers to the arrangement according to the invention of a spectrally tuned shortwaved source of illumination and a camera that serves for recognizing defects inside the transparent protective layer as well as for recognizing areas where the protective layer is completely absent.

According to the preferred embodiment, cameras are employed to scan laminate floor coverings by an imaging technique. Naturally, the inventive idea is not restricted to the use of cameras, but rather, it encompasses all types of imaging sensors, particularly also scanners that scan the laminate surface in a punctiform manner, so-called optical contact line sensors and other imaging sensors of the type known to the person skilled in the art of optics and image processing.

Figure 1:
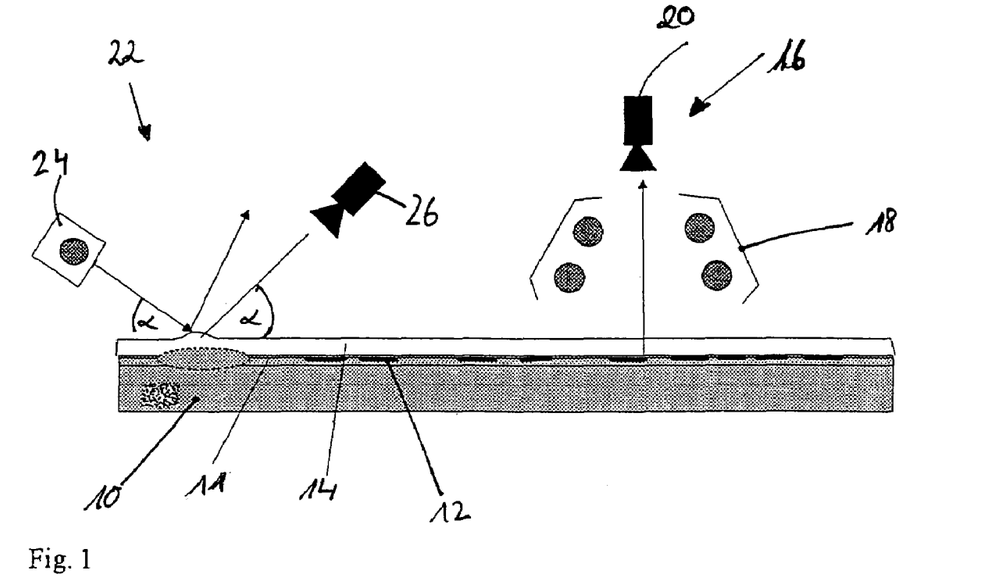
FIG. 1 schematically shows an arrangement comprising a color line camera, diffuse incident illumination and a black-and-white line camera that picks up the reflected light coming from a directed source of illumination.

FIG. 1 shows a simplified form of a typical laminate structure having a substrate material 10 (in the case of floor laminates, usually a medium-density or high-density fiberboard and in the case of laminates made of plastic, a plastic film that is several millimeters thick). A paper or plastic film 11 whose surface 12 has the typical look, for example, of a wood structure, or is a marble or natural-stone imitation, is applied onto this substrate. This is followed by a transparent protective layer 14, the so-called overlay film, which forms a hard, durable and abrasion-proof laminate surface.

It is a known procedure, for example, to employ systems for inspecting ceramic tiles (CeraVision®, manufactured by MASSEN machine vision systems GmbH) in order to detect defects in the decor by using a color camera and computer-aided color image evaluation. For this purpose, the surface is diffusely illuminated with a source of white light and the local color patterning is compared to color statistics previously acquired from a reference. This arrangement is referred to as "color channel". Such an arrangement is designated with the reference numeral 16 in FIGS. 1 and 2. The source of white light has been given the reference numeral 18 and the color camera has the reference numeral 20.

It is likewise a known procedure, for instance, from the inspection of ceramic tiles, to additionally illuminate the surface with a directed source of light and to make the observation with a black-and-white camera that detects the surface at the same angle. As a result, all of the defects on the surface of the protective layer are detected that either reflect the illuminating beam of light at an angle other than the angle of incidence (for instance, bumps or dents) or that reflect the beam of light at the same angle but with a different intensity (for example, places that are locally too dull or too glossy). This arrangement is referred to as "reflection channel". Such an arrangement is indicated by the reference numeral 22 in FIGS. 1 and 2. The source of light has the reference numeral 24 and the black-and-white camera has the reference numeral 26. In this embodiment, the source of light 24 and the black-and-white camera 26 are arranged at the same angle α relative to the surface of the laminate.

Figure 2:
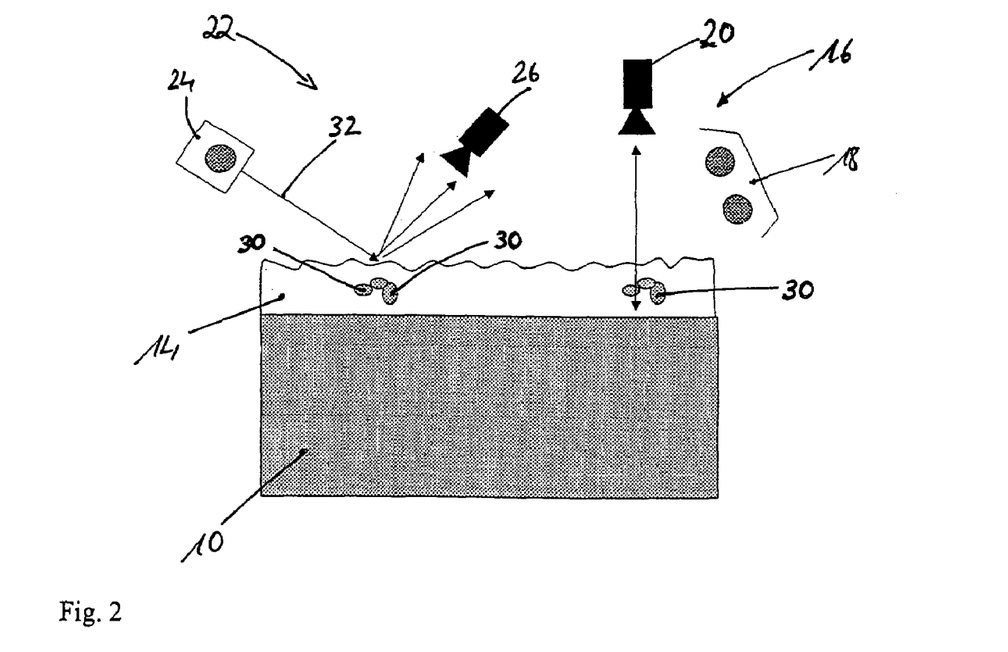
FIG. 2 schematically depicts a cross section through an embossed laminate floor covering provided with a transparent protective layer in order to show that defects inside the protective layer cannot be detected either by the so-called reflection channel or by the so-called color channel.

Defects 30 inside the protective layer 14, as shown in FIG. 2, are not recognized by the reflection channel 22 since the illuminating beam of light 32 is already reflected off the surface. Even localized absences of overlay (so-called overlay flaking) are often not recognized by the reflection channel 22, particularly in the case of laminates having a randomly embossed surface, which generates a high level of background noise.

As a rule, typical defects 30 such as, for example, slight milkiness and melanin spots inside the protective layer 14, are likewise not recognized by the color camera 20 since these defects 30 only slightly change the local colors observed through the transparent protective layer 14, so that, in spite of these defects 30, these still match the color statistics previously acquired. Since many laminate surfaces consist of random patterns and the printing of the decor film is created randomly by intentionally shifting the printing cylinders as well as by an intentional lack of synchronization among the individual inking units, it is not possible to make a direct image-to-image comparison, but rather, it is necessary to use the model of a statistical color pattern distribution.

Therefore the prior-art surface-inspection methods are not capable of recognizing defects 30 inside the transparent protective layer 14. In the case of embossed laminates, even a completely absent overlay cannot be reliably recognized.

According to the present invention, the laminate surface can be detected by imaging in such a way that defects 30 inside the transparent protective layer 14 ranging all the way to the complete localized absence of the protective layer 14 can be recognized with high reliability for both embossed and non-embossed laminates. For this purpose, according to the invention, two different physical effects are utilized.

Figure 3:
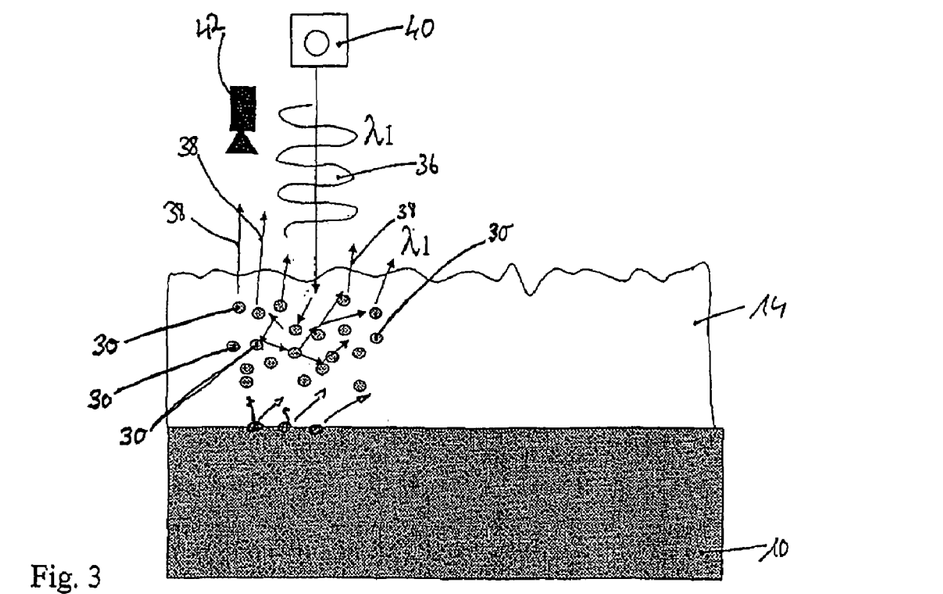
FIG. 3 shows, by way of an example, that slight milkiness defects inside the embossed, transparent protective layer are detected if the latter is diffusely illuminated with shortwaved light and the scattered light is picked up by an imaging technique.

As shown in FIG. 3, the milkiness of the transparent protective layer 14 (which results, for instance, from an inadequate compressing temperature and compressing force) can be described as a scatter model. The individual, nontransparent microscopic particles 30 scatter the penetrating light 36 and reflect a large fraction 38 back into the observing camera. If the microscopic particles 30 are small in comparison to the wavelength $\lambda_1$ of the scattered light, as is the case here, the scatter inside a material rises by a power of four of the inverse value of the wavelength:

$$I(\text{scatter}) \sim 1/\lambda^4.$$

Therefore, according to the invention, a source of illumination 40 having a wavelength range $\lambda_1$ is selected which is as shortwaved as possible. This is advantageously the blue region that directly follows the ultraviolet region that can no longer be detected by the camera. Preferably, the camera 42 that detects the back-scattered light 38 is equipped with an optical bandpass filter that only allows the passage of the wavelength range $\lambda_1$ of this range that is optimized with respect to the scatter inside the protective layer 14 and that blocks all extraneous light of a different color. Preferably, in order to detect the scatter, the camera 42 is arranged perpendicularly above the laminate and the illumination 40 is likewise arranged perpendicularly so as to minimize the effect of any embossing of the surface. According to the invention, the shortwaved source of illumination 36 is configured so as to be at least partially diffuse in order to minimize the optical effect on the detected scatter image caused by the surface embossing.

With this method and this arrangement, all defects 30 inside and beneath the transparent protective layer 14 (in the example of the laminate floor covering of FIG. 2, on the interface between the transparent protective layer and the printed paper or plastic film) can be detected that are due to scatter effects inside and beneath the transparent protective layer 14. Scattering particles beneath the protective layer can come, for example, from melanin residues that have remained between the transparent overlay film and the colored decor paper.

Whereas scattering particles inside the transparent protective layer scatter back the penetrating, diffuse, shortwaved light, this effect also causes a widening of the image of a front-projected light line through a halo of light that grows with the scatter. This effect is referred to as "light halo effect" in the above-mentioned German patent specification DE 196 09 045 C1 and is employed there to measure the local hardness of a wood surface.

In a preferred embodiment of the method according to the invention, the light from the source of illumination by means of which the defects inside the transparent protective layer are to be detected is imaged in the form of a line on the surface of the transparent protective layer. The back scatter in the area of the defective places causes the line to widen in these areas. This widening is detected by the imaging sensor that is associated with this source of illumination such as, for instance, a black-and-white camera. Defective places can be ascertained in this manner.

The complete absence of the transparent protective layer 14 cannot be detected with the scatter effect. Particularly in the case of embossed surfaces, this can likewise not be detected with the reflection channel 22 since the embossed surface generates a background noise that superimposes the difference between the gloss detected when a protective layer 14 is present and the lower gloss of the illuminated decor paper 12 when the protective layer 14 is absent.

Figure 4:
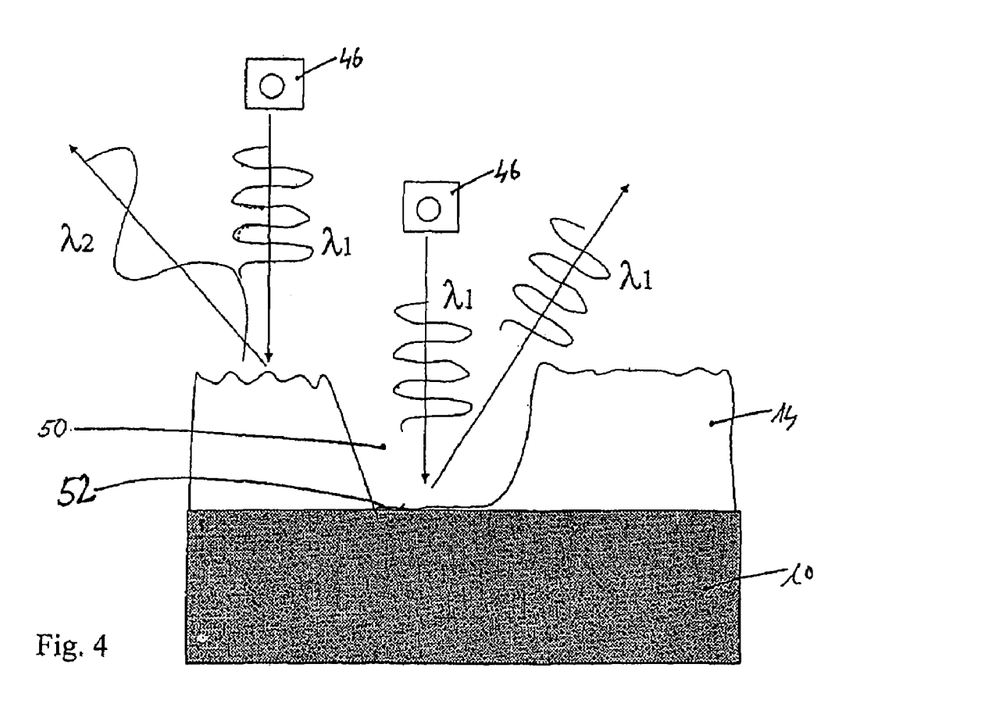
FIG. 4 shows, by way of an example, that local tears in the transparent protective layer can be detected by imaging on the basis of the localized absence of fluorescence on the surface illuminated with radiation near the UV spectrum, without the mechanical embossing interfering with the recognition.

According to the invention, as shown in FIG. 4, the fluorescence of the protective layer 14 is utilized for this purpose. In order to do so, the surface is irradiated with shortwaved light from a source of illumination 46 whose wavelength range $\lambda_1$ is at the lower end of the sensitivity of the observing camera. The fluorescence of the intact protective layer 14 gives rise to a back-scattered light having a larger wavelength 2 that lies in the more sensitive range of the observing camera. The protective layer 14 thus appears as slightly bright.

Absent places 50, so-called overlay flaking, are, in contrast, dark since the reflecting decor paper 52 does not exhibit any fluorescent properties and therefore the back-scattered light has the same wavelength $\lambda_1$ as the light emitted by the source of illumination 46.

Absent places of the transparent protective layer can also be recognized in that the shortwaved light emitted by the source of illumination is imaged in the form of a line on the surface to be inspected. In areas where the surface having a color pattern is covered by the transparent protective layer, the fluorescent light emitted by the protective layer alters the image of the line projected onto the surface. If the sensitivity of the detecting camera in the range of the fluorescent light is greater than in the range of the exciting light, the line appears brighter in areas that are covered by the protective layer than in areas that are not covered by the protective layer.

Preferably, so-called black-light lamps which have an ultraviolet fraction that excites the fluorescence of the protective layer and which also emit a shortwaved visible fraction are employed to illuminate the laminate surface. In this manner, a single source of illumination and a single camera 41 (also see FIG. 6a) can use the localized higher scatter to recognize the milkiness defects inside the transparent protective layer as bright image places, and they can use the localized absence of fluorescence to recognize the localized absence of the transparent protective layer as dark image places on the overall slightly bright background.

Figure 5:
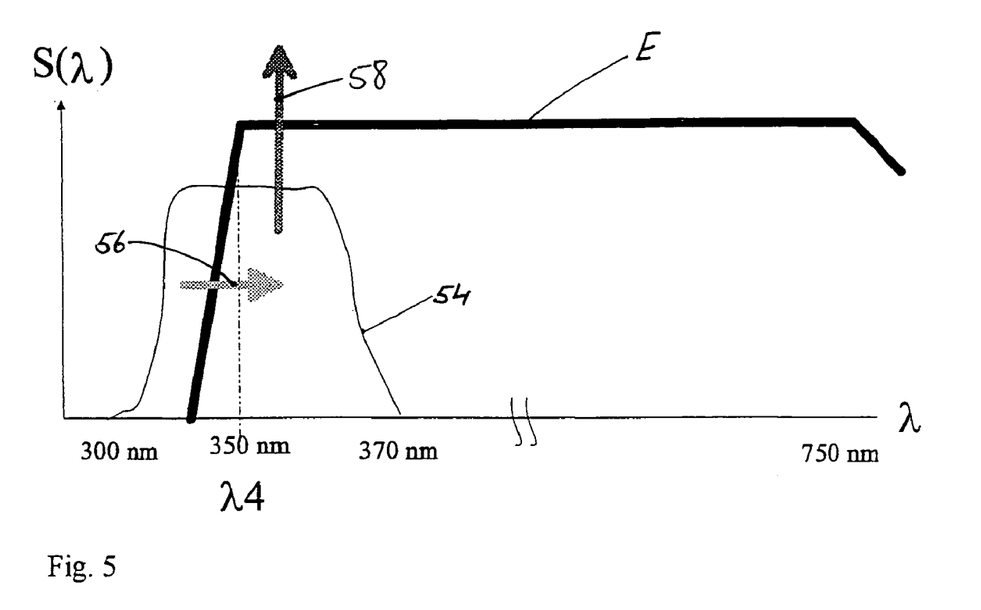
FIG. 5 schematically shows the emission spectrum of a source of illumination by means of which the transparent protective layer can be simultaneously excited to fluorescence and defects inside the transparent protective layer can be detected through the wavelength-dependent scatter at scatter centers inside the protective layer, together with the sensitivity characteristic line of the associated imaging sensor.

FIG. 5 schematically shows the spectrum $S(\lambda)$ of the source of illumination 41 together with the sensitivity characteristic line E of the camera, which are necessary to detect defects 30 inside the protective layer 14 ranging all the way to the complete absence of the protective layer 14 through the simultaneous use of scatter and fluorescence.

The shortwaved black-light source of illumination has, for example, the spectral emission characteristic line that is centered around the medium wavelength $\lambda_4$. The observing black-and-white camera has a sensitivity characteristic line E that ranges from shortwaved blue all the way to red. For the sake of simplicity, this characteristic line E is considered to be constant up to the important rising branch at 350 nm.

The fluorescence of the protective layer 14 shifts the spectral wavelengths that are invisible or less sensitive for the camera into the range of higher sensitivity of the camera, as indicated by the arrow 56. The intact protective layer appears here as slightly bright and the absent protective layer appears dark. The scatter caused by milky melanin particles in the protective layer enlarges the reflection in the shortwaved violet-blue of the source of illumination, as indicated by the arrow 58. Consequently, melanin spots and slight milkiness appear as markedly brighter zones.

Figure 6A:
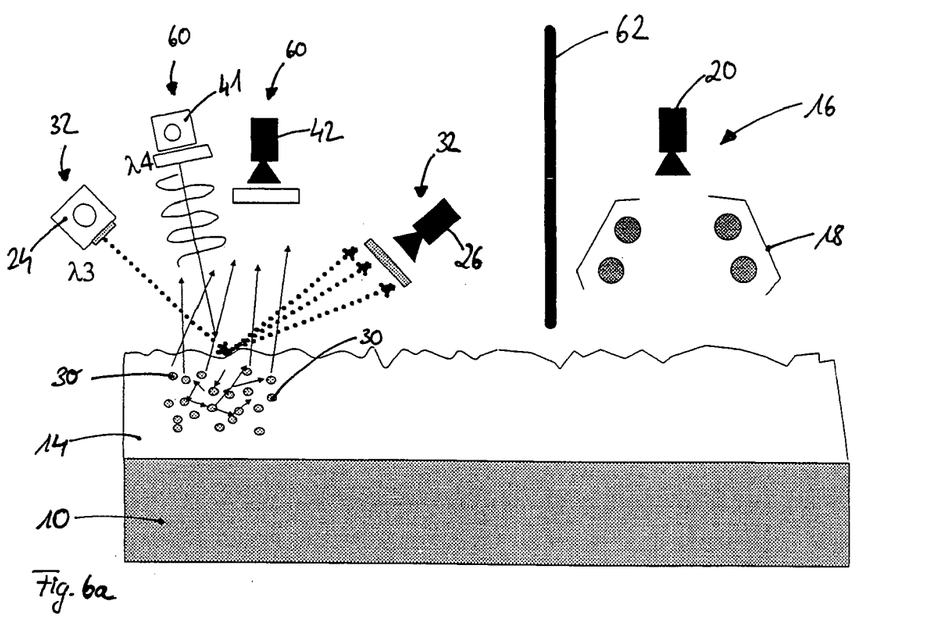
FIGS. 6a and 6b show, by way of an example, how to optically insulate the various sources of illumination from the cameras associated with the sources of illumination, once through shielding and once through a different spectral configuration of the wavelength range of the so-called reflection channel and of the so-called "overlay channel".

FIG. 6a shows by way of an example an arrangement according to the invention of the three image channels, namely, the "color channel" 16, the "reflection channel" 32 and the "overlay channel" 60. The optical insulation between the color channel 16 and the other two channels 32 and 60, respectively, is achieved by a shielding 62 of the diffuse white light. In order to keep the installation dimensions on the production line as small as possible, according to the invention, the optical insulation of the reflection channel 32 and the overlay channel 60 is achieved by a spectral separation of the reflection illumination and the overlay illumination. The directed source of illumination 24 of the reflection channel 32 is configured for a wavelength range 3 (also see FIG. 6b) that does not intersect with the shortwaved range $\lambda_4$ of the source of illumination 41 of the overlay channel 60.

Figure 6B:
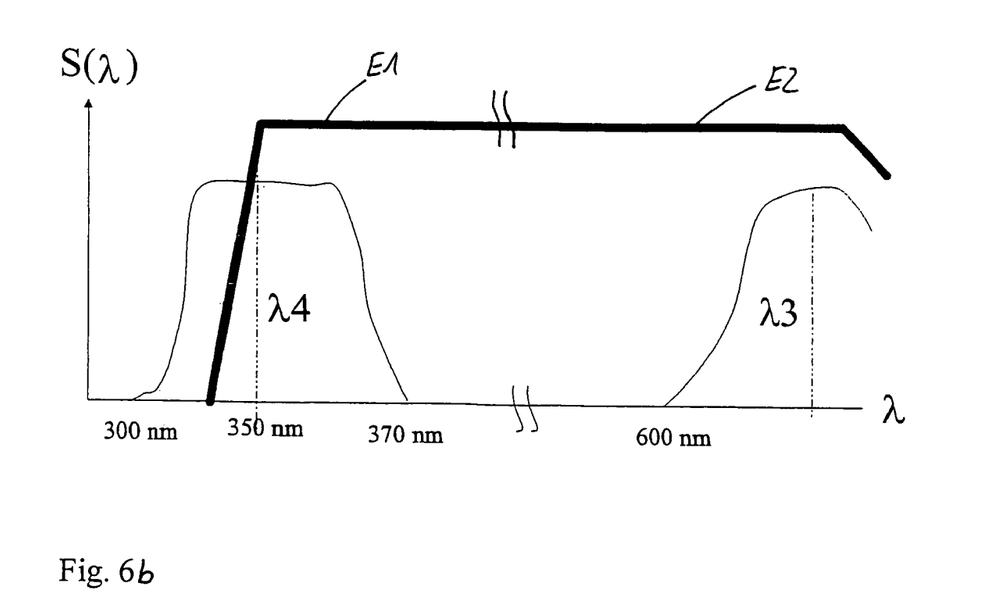

Consequently, $\lambda_3$ is preferably moved into the red or near-infrared range. At the same time, the camera 26 of the reflection channel 32 is equipped with an optical bandpass filter having the same pass-band $\lambda_3$ in order to become insensitive to the illumination of the overlay channel. Analogously, the camera 42 of the overlay channel 60 is equipped with an optical filter having the pass-band $\lambda_4$, which only allows the shortwaved back refraction and fluorescence to pass through. These conditions are once again depicted in the spectral diagram of FIG. 3b, whereby the sensitivity characteristic line is divided in accordance with the emitted spectrum into two parts E1 and E2, each corresponding to the appertaining sensitivity range E1 or E2 of the camera 42 of the overlay channel 60 and of the camera 26 of the reflection channel 32.

According to the invention, this spectral separation brings about two decisive advantages: the geometrical installation dimensions are markedly reduced and the two channels, namely, "reflection" and "overlay" observe the same place of the laminate. Consequently, their image signals can be combined in the manner of multisensorial and multidimensional signal processing to form a 2-channel image signal and they can be evaluated by means of the method of multidimensional pattern recognition. This multidimensional image processing has already been described in the above-mentioned German patent specification DE 196 09 045 C1.

The explanation of the inventive idea on the basis of smooth wood laminate surfaces and the use of cameras do not mean that the inventive idea is limited to these materials and these imaging means. It is obvious for the person skilled in the art of image processing to employ this inventive idea and the arrangement for other colored surfaces consisting of other materials with transparent protective layers which can be smooth as well as not smooth and also to employ imaging means other than cameras. The present invention can likewise be employed for optical surface inspection systems with 3D-channels, X-ray channels and the like, which inspect surfaces that are provided with transparent protective layers.

The invention claimed is:

1. A method for the optical inspection of a transparent protective layer and of a colored patterned surface, whereby the transparent protective layer at least partially covers the colored patterned surface, said method using a first source of illumination and a first imaging sensor associated with the first source of illumination, said method comprising the steps of:

illuminating said protective layer with light emitted by the first source of illumination in order to recognize defective places inside and beneath the transparent protective layer, said first source of illumination emitting short-waved light in the range that is visible for the first imaging sensor and that is at least partially diffuse, the light striking said surface penetrating at least partially into the protective layer and scattering at the defective places;

picking up light scattered back from the defective places with the first imaging sensor; and recognizing the defective places by the local increase in the intensity of the light picked up by the first imaging sensor in the area of the defective places.

2. The method according to claim 1, wherein the first imaging sensor associated with the first source of illumination is essentially only sensitive to light emitted in the wavelength range of the first source of illumination.

3. The method according to claim 1, wherein the first source of illumination and the first imaging sensor associated with the first source of illumination are arranged perpendicularly above the surface of the transparent protective layer.

4. The method according to claim 1, wherein the defective places in the transparent protective layer are turbid places.

5. A method for the optical inspection of a transparent protective layer and of a colored patterned surface, whereby the transparent protective layer at least partially covers the colored patterned surface, said method using a first source of illumination and a first imaging sensor associated with the first source of illumination, said method comprising the steps of:

illuminating said protective layer with light emitted by the first source of illumination in order to recognize defective places inside and beneath the transparent protective layer, said first source of illumination emitting short-waved light in the range that is visible for the first imaging sensor, the light striking said surface penetrating at least partially into the protective layer and scattering at the defective places:

picking up light scattered back from the defective places with the first imaging sensor; and recognizing the defective places by the local increase in the intensity of the light picked up by the first imaging sensor in the area of the defective places;

the light emitted by the first source of illumination being imaged in the form of a line on the surface of the transparent protective layer and the widening of the line caused by the back-scattered light in the area of the defective places being detected on the surface of the protective layer by the first imaging sensor.

6. A method for the optical inspection of a transparent protective layer and of a colored patterned surface, whereby the transparent protective layer at least partially covers the colored patterned surface, said method using a first source of illumination and a first imaging sensor associated with the first source of illumination, said method comprising the steps of:

illuminating said protective layer with light emitted by the first source of illumination in order to recognize defective places inside and beneath the transparent protective layer, said first source of illumination emitting short-waved light in the range that is visible for the first imaging sensor, the light striking said surface penetrating at least partially into the protective layer and scattering at the defective places;

picking up light scattered back from the defective places with the first imaging sensor;

recognizing the defective places by the local increase in the intensity of the light picked up by the first imaging sensor in the area of the defective places;

providing a second source of illumination that emits light at a first wavelength that excites the protective layer to fluoresce with light at a second wavelength that is different from the first wavelength, the fluorescent light being picked up by a second imaging sensor associated with the second source of illumination, and defective places in the transparent protective layer being recognized on the basis of local changes in the intensity of the fluorescent light.

7. The method according to claim 6, wherein the second imaging sensor associated with the second source of illumination has greater sensitivity in the wavelength range of the second wavelength than in the wavelength range of the first wavelength.

8. The method according to claim 6, wherein the light emitted by the second source of illumination is imaged in the form of a line on the surface of the transparent protective layer and the change in the intensity of the line on the surface of the transparent layer caused by changes in the intensity of the fluorescent light is detected by the second imaging sensor.

9. The method according to claim 6, wherein the defective places are areas on the colored patterned surface which are not covered by the transparent protective layer.

10. The method according to claim 6, wherein a single source of illumination is employed as the first source of illumination and as the second source of illumination.

11. The method according to claim 1, wherein color defects in the colored patterned surface are detected by a color-capable imaging sensor.

12. The method according to claim 6, wherein, in order to detect defects on the surface of the transparent protective layer, a third source of illumination emits a directed beam of light that is reflected off the surface of the protective layer, said reflected light being picked up by a third imaging sensor associated with the third source of illumination, and the defects on the surface of the transparent protective layer are recognized on the basis of changes in the intensity of the light picked up by the third imaging sensor.

13. The method according to claim 12, wherein said first, second and third imaging sensors with their associated sources of illumination are shielded from each other.

14. The method according to claim 13, wherein said first, second and third imaging sensors with their associated sources of illumination are shielded from each other in that they operate at different, non-overlapping wavelength ranges.

15. The method according to claim 14, wherein a single source of illumination is employed as the first source of illumination and as the second source of illumination and said single source of illumination and the third source of illumination emit light in different, non-overlapping wavelength ranges and the first and third imaging sensors associated with the first and third sources of illumination are sensitive in different, non-overlapping wavelength ranges.

16. The method according to claim 1, wherein the colored patterned surfaces and the transparent protective layer are parts of laminate floor covering elements, whereby these laminate floor covering elements comprise wood or plastic substrate elements onto which multi-colored printed films with a colored patterned surface are arranged and which are covered by a transparent protective layer.

17. The method according to claim 1, wherein the surface of the transparent protective layer is provided with an embossed structure.

18. An arrangement for the optical inspection of a transparent protective layer and of a colored patterned surface, whereby the transparent protective layer at least partially covers the colored patterned surface, said arrangement comprising a first source of illumination and a first imaging sensor associated with the first source of illumination, the emission spectrum of the first source of illumination encompassing shortwaved light that is visible for the first imaging sensor and said source of illumination being configured so as to emit light that is at least partially diffuse, the first imaging sensor picking up light scattered back from defective places inside and beneath the transparent protective layer, and the defective places can be recognized by the local increase in the intensity of the light picked up by the first imaging sensor in the area of the defective places.

19. An arrangement for the optical inspection of a transparent protective layer and of a colored patterned surface, whereby the transparent protective layer at least partially covers the colored patterned surface, said arrangement comprising a first source of illumination and a first imaging sensor associated with the first source of illumination, the emission spectrum of the first source of illumination encompassing shortwaved light that is visible for the first imaging sensor, the first imaging sensor picking up light scattered back from defective places inside and beneath the transparent protective layer, whereby the defective places can be recognized by the local increase in the intensity of the light picked up by the first imaging sensor in the area of the defective places, a second source of illumination arranged at a distance from the transparent protective layer to be inspected, the second source of illumination emitting light at a first wavelength that excites the protective layer to fluoresce with light at a second wavelength that is different from the first wavelength, and a second imaging sensor associated with the second source of illumination arranged in such a way that it can pick up the fluorescent light of the protective layer, whereby defective places in the transparent protective layer can be recognized by local changes in the intensity of the fluorescent light.

20. The arrangement according to claim 18, wherein a color-capable imaging sensor is provided for detecting color defects in the colored patterned surface.

21. The arrangement according to claim 19, wherein a third source of illumination is arranged at a distance from the transparent protective layer to be inspected and a third imaging sensor associated with the third source of illumination is arranged at a distance and at the same angle as the third source of illumination in terms of the protective layer to be inspected, said third imaging sensor, for purposes of detecting defects on the surface of the protective layer, picks up the light that has been emitted by the third source of illumination and that has been reflected off the surface of the protective layer.

22. The arrangement according to claim 21, wherein a color-capable imaging sensor is provided for detecting color defects in the colored patterned surface and said color-capable imaging sensor, said first and third imaging sensors with their associated sources of illumination are optically shielded from each other.

23. The arrangement according to claim 19, wherein a color-capable imaging sensor is provided for detecting color defects in the colored patterned surface.

* * * * *